(12) United States Patent
Morris

(10) Patent No.: US 6,421,561 B1
(45) Date of Patent: Jul. 16, 2002

(54) RATE ADJUSTABLE DRUG DELIVERY SYSTEM

(75) Inventor: Russell L. Morris, Lindstrom, MN (US)

(73) Assignee: Birch Point Medical, Inc., Oakdale, MN (US)

( * ) Notice: Subject to any disclaimer, the term of this patent is extended or adjusted under 35 U.S.C. 154(b) by 0 days.

(21) Appl. No.: 09/613,984

(22) Filed: Jul. 11, 2000

Related U.S. Application Data

(60) Provisional application No. 60/173,710, filed on Dec. 30, 1999.

(51) Int. Cl.⁷ .................................................. A61N 1/30
(52) U.S. Cl. ............................................................ 604/20
(58) Field of Search ..................... 604/20, 501; 607/149

(56) References Cited

U.S. PATENT DOCUMENTS

| | | |
|---|---|---|
| 116,562 A | 7/1871 | Collins |
| 175,974 A | 4/1876 | Hall |
| 222,276 A | 12/1879 | Hunter |
| 385,556 A | 7/1888 | Hoke |
| 393,741 A | 12/1888 | Collins |
| 770,014 A | 9/1904 | Linn |
| 857,664 A | 6/1907 | Overman |
| 4,619,252 A | 10/1986 | Ibbott |
| 4,713,050 A | 12/1987 | Sibalis |
| 4,722,726 A | 2/1988 | Sanderson et al. |
| 4,747,819 A | 5/1988 | Phipps et al. |
| 4,752,285 A | 6/1988 | Petelenz et al. |
| 4,767,401 A | 8/1988 | Seiderman |
| 4,927,408 A | 5/1990 | Haak et al. |
| 4,950,229 A | 8/1990 | Sage, Jr. |
| 5,135,477 A | 8/1992 | Untereker et al. |
| 5,160,315 A | 11/1992 | Heinecke et al. |
| 5,162,042 A | 11/1992 | Gyory et al. |
| 5,203,768 A | 4/1993 | Haak et al. |
| 5,221,254 A | 6/1993 | Phipps |
| 5,254,081 A | 10/1993 | Mauer et al. |
| 5,295,979 A | 3/1994 | DeLaurentis et al. |
| 5,298,017 A | 3/1994 | Haak et al. |
| 5,320,731 A | 6/1994 | Muller et al. |
| 5,322,520 A | 6/1994 | Milder |
| 5,354,321 A | 10/1994 | Berger |
| 5,356,632 A | 10/1994 | Gross et al. |
| 5,358,483 A | 10/1994 | Sibalis |
| 5,403,275 A | 4/1995 | Phipps |
| 5,405,317 A | 4/1995 | Myers et al. |
| 5,431,625 A | 7/1995 | Fabian et al. |

(List continued on next page.)

FOREIGN PATENT DOCUMENTS

| | | |
|---|---|---|
| DE | 1967927 | 7/1934 |
| DE | 2263792 | 3/1974 |
| EP | 0060451 | 3/1982 |
| EP | 0308572 | 8/1984 |
| EP | 456 122 | 5/1991 |
| EP | 0 893 139 | 7/1998 |
| EP | 0 893 139 A | 1/1999 |
| FR | 2 263 792 A | 10/1975 |
| GB | 410009 | 5/1934 |
| GB | 2.206493 | 1/1989 |
| GB | 0456122 | 11/1995 |
| WO | WO 01/49365 | 7/2001 |

OTHER PUBLICATIONS

"Iontophoresis: Applications in Transdermal Medication Delivery", Physical Therapy, vol. 75, No. 6, Jun. 1995, pp. 554–563.

"Transdermal Iontophoresis. Part I: Basic Principles and Considerations", Methods Find Exp Clin Pharmacol, 1999, 21 (2) : 139–151.

Primary Examiner—Mark Bockelman
(74) Attorney, Agent, or Firm—Nikolai & Mersereau, P.A.

(57) ABSTRACT

A transdermal iontophoretic therapeutic agent delivery system which is provided with a plurality of self-contained serially connected galvanic sources.

18 Claims, 8 Drawing Sheets

U.S. PATENT DOCUMENTS

| | | |
|---|---|---|
| 5,458,569 A | 10/1995 | Kirk, III et al. |
| 5,466,217 A | 11/1995 | Myers et al. |
| 5,533,971 A | 7/1996 | Phipps |
| 5,605,536 A | 2/1997 | Sibalis |
| 5,651,768 A | 7/1997 | Sibalis |
| 5,685,837 A | 11/1997 | Horstmann |
| 5,759,564 A | 6/1998 | Milder et al. |
| 5,772,688 A | 6/1998 | Muroki |
| 5,983,130 A | 11/1999 | Phipps et al. |

RATE ADJUSTABLE DRUG DELIVERY SYSTEM

This application is a complete application claiming priority based on provisional application No. 60/173,710, filed Dec. 30, 1999, and entitled Rate Adjustable Drug Delivery System.

BACKGROUND OF THE INVENTION

I. Field of the Invention

The present invention concerns transdermal delivery of therapeutic agents by use of an applied electromotive force, commonly known as iontophoresis. More particularly, the invention is directed to a system for iontophoresis that is self contained, quantitatively self limiting, and in which the delivery rate is variable or adjustable. The system is contained preferably in a rather small skin worn patch which contains electrodes and a therapeutic agent. When applied to the skin, the system completes a circuit and spontaneously initiates the flow of a galvanic current of measured, limited duration corresponding to the desired amount of therapeutic agent to be delivered. The system may be anode or cathode limited.

II. Related Art

The process of iontophoresis was described by LeDuc in 1908, and has since found commercial use in the delivery of ionically charged compounds such as pilocarpine, dexamethasone, and lidocaine. In this delivery method, ions bearing a positive charge are driven across the skin at the site of an electrolytic electrical system anode, while ions bearing a negative charge are driven across the skin at the site of an electrolytic electrical system cathode.

With iontophoretic devices, the application time and level of current flow (usually reported in units of milliamp-minutes) between the anode and cathode is directly correlated to the amount of drug delivered. The efficiency of drug delivery in an iontophoretic system can be measured by the proportion of current carried by the drug molecule, relative to the current carried by competing non-medication ions having the same charge as the medication.

At present, iontophoresis devices are conventionally comprised of two electrodes attached to a patient, each connected via a wire to a microprocessor controlled electrical instrument. Medication is placed under one or both of the electrodes, for delivery into the body as the instrument is activated. The instrument is designed to regulate current flow and application time. Examples of such instruments are described in U.S. Pat. Nos. 5,254,081, and 5,431,625. Power for these devices is usually provided by DC batteries, which when providing power for the microprocessor controlled circuitry allow application of a voltage to the electrodes to create a regulated current flow. The automated control of current flow and time (milliamp-minutes) is of great advantage, in order to prevent excessive dosages of therapeutic agents from being delivered. However, these battery powered microprocessor systems are disadvantaged by the fact that patients are 'attached by wire' to an instrument, which limits patient mobility and ability to conduct normal daily activities. A typical application period is approximately 20 minutes to 2 hours, which consumes instrument, caregiver, and patient time.

A significant advantage of a microprocessor controlled iontophoretic system is an ability to adjust electrical current as a function of time, while the system is being used. For example, to administer medication quickly into systemic circulation, an initial high flow rate is desired. However, adjustment to a lower flow rate may be desired afterward for optimal maintenance of a particular plasma medication level.

More recently, wearable iontophoretic systems have been developed in which the electrical circuitry and power supplied are integrated into a single patch. These systems are advantageous in that they do not require external wires, and they are much smaller in size. Examples of such systems can be found in U.S. Pat. Nos. 5,358,483; 5,458,569; 5,466,217; 5,605,536; and 5,651,768. However, these systems also have drawbacks. They are relatively inflexible and expensive, owing to the requirements of multiple electronic components, battery power supplies and electrical interconnects.

Power to drive iontophoretic current flow can also be supplied by galvanic means, which utilizes dissimilar anode and cathode materials to produce a spontaneous current flow when they are contacted with the body. These systems hold advantage, in that separate electrical circuitry and battery sources are not required. An iontophoretic device, not of the transdermal type, but one which utilizes galvanic means is described in U.S. Pat. No. 5,322,520, which describes an implanted device designed to deliver oligodynamic metal ions from its surface, in order to kill bacteria on or near it.

Devices suggesting galvanic power as a means to transdermally deliver medication are described in U.S. Pat. Nos. 5,162,042, and 5,405,317. These devices are disadvantaged by the fact that the amount of medication delivered is not automatically regulated, and they require a timely removal of the device from the body to prevent a potentially toxic over-dosage of medication.

In a co-pending application PCT/US99/18861, designating the U.S., claiming priority based on U.S. provisional application No. 60/098,652, assigned to the same Assignee as the present application, an iontophoresis patch system is described which uses galvanic power and provides a known dosage capacity. Thus, this system can be designed to automatically shut off after a specified dosage, and the risk of overdosage is eliminated. That co-pending application is deemed incorporated herein by reference for any purpose.

Horstmann, in U.S. Pat. No. 5,685,837, describes a transdermal therapeutic system which uses series mounted sheet-like galvanic elements as a power source. That device has an ability to either create a constant intensity of current using a high internal resistance element, or create a gradual decreasing current intensity using a low internal resistance element. The low internal resistance, and a decreasing current flow, is caused by a build up of ions into an electrolyte layer of the galvanic element.

While it appears advantageous, there are certain practical disadvantages to the Horstmann system. To achieve a decreasing current, a very thin electrolyte layer required. The thin layer is susceptible to mechanical failure during production or use. Also, rather than the gradual decreasing current of the Horstmann system, a steady high rate of current which then rapidly falls is optimal, so that a known charge dosage can be administered in minimal time. The actual charge dosage administered using the Horstmann device is not accurately known, since a nernstian decline in voltage is in a non-linear diminishing rate, and thus the system will not fall to zero current during practical time scales.

One restriction of all galvanic systems is a limited supply of user-friendly materials which can be practically used. Many materials may be toxic themselves, and/or they may be difficult to work with in the manufacturing process. A significant problem lies with materials that are reactive with water, and therefore can alter the pH of the medication solution during use. pH changes can harm skin, or cause adverse reaction with medication. For example, we have found zinc ($E^0=-2.37$) to be an excellent galvanic material, but magnesium ($E^0=-2.37$) causes a pH change in iontophoretic medication chambers. Silver chloride ($E^0=+0.222$) does not affect pH of a medication chamber, but manganese dioxide ($E^0=+1.23$) does. Consequently, the voltages obtainable in galvanically powered systems are limited by material stability or compatibility. Of course, various other species may have application as oxidizable or reducible species under different circumstances.

Another restriction or limitation of galvanically powered systems is an inability to increase or decrease voltage (and medication delivery) during use. The voltage is fixed by the galvanic ½ reactions used, and cannot be altered in process. This is a significant disadvantage in circumstances where increasing rate of delivery, such as to administer a bolus of medication, is desired. Accordingly, it would present a great advantage were increased potential available in such a device.

A primary object of the invention is to provide a galvanically powered iontophoretic device which can provide any desired time-voltage profile (and consequently customize the rate profile of medication delivery) using materials which are non-pH reactive in contact with water, and stable when used in the in a manufacturing process.

A further object of the present invention is to provide an iontophoretic device which can provide any desired time-voltage or delivery profile using circuit components without requiring a microprocessor.

Another object of the invention is to provide an iontophoretic device capable of maintaining voltage at a stable level for a known charge dosage, afterwards having an automated ability to adjust the voltage downward or upward to at least a second known voltage in rapid fashion, without requiring an integrated microprocessor.

It is a still further object of the invention to provide a galvanically powered system which can be adjusted to higher voltage during use, in order to administer a bolus of medication.

Still another object of the invention is to provide a galvanically powered system in which the potential level can be made time variable by employing several serially connected galvanic sources of different coulombic capacities in conjunction with parallel connected resistor devices.

Other objects and advantages will occur to those skilled in the art upon familiarization with this specification, drawings and appended claims.

SUMMARY OF THE INVENTION

An iontophoretic patch in accordance with the invention includes in its simplest form at least three chambers: a cationic drug chamber, an anionic drug chamber, and an additional galvanic source or cell. The system may also have a series of such cells together with one or more parallel connected resistance devices or other components in more complex versions. In the cationic drug chamber, an electrode is contained which includes or is coated with, an electrochemically oxidizable species. In the anionic drug chamber, an electrode is contained which includes or is coated with, an electrochemically reducible species. The chambers are separated by a known distance optimally between 0.1 and 2 cm. The cationic chamber electrode and the anionic chamber electrode are connected by electrically conductive elements to an additional intermediate electrochemical cell or cells. Opposing ends of the electrically conductive elements, which extend to the intermediate cell or cells, are comprised of, or coated with, reductive species if the end opposite is oxidative, or oxidative species if the end opposite is reductive.

The net result is a series connection of galvanic couples or sources, which serve to boost the applied potential of the iontophoretic system. Embodiments employing an illustration of an iontophoretic system using zinc as the oxidative species and silver chloride as the reducible species, having one intermediate chamber or galvanic source and providing an applied potential of approximately 2 volts and also using two intermediate chambers or galvanic sources and providing an applied potential of approximately 3 volts are shown in the drawings to illustrate the concept without limitation. The total applied potential of the galvanic system of this invention is directly correlated to the number of intermediate chambers utilized. It will be apparent that the number of intermediate galvanic sources or couples can be varied depending on the desired total potential.

In addition, one or more resistor devices can be connected in parallel with one or more of the galvanic sources. This assures serial operation of multiple source systems while all sources are operating and provides paths across depleted cells of lesser capacity in the system so that a therapeutic agent can continue to be administered to a lower rate.

In addition, one or more switching devices can be provided in the iontophoretic patch to switch one or more of the intermediate sources or chambers into the circuit or to bypass or shunt one or more galvanic sources as desired. A switching device rather than a resister can also be used to by-pass a depleted galvanic source without added circuit resistance if it is desired to provide an initial bolus of therapeutic material, all serially connected sources or cells can be employed for an initial period and one or more configured to deplete and thereby reduce the potential at a later time.

Thus, one or more of the intermediate chambers can be made anode or cathode limited in a manner which causes depletion at a time when the desired bolus of initial material has been delivered. Parallel resistors or switches, then, provide a conductive path to enable delivery to continue at a lower rate. Switching devices can also be employed which shut off the entire galvanic flow in the iontophoretic patch or to switch in additional series connected galvanic sources as by opening by-pass conductor circuits for example.

In yet another type of configuration, galvanic sources can be serially connected in opposed polarity such that a lower capacity source opposes a therapeutic or agent delivery source to initially delay agent delivery until the lower capacity source is depleted.

The oxidizable species and the reducible species are selected so as to provide a spontaneous galvanic potential and current flow when the iontophoretic patch is in contact with the body. An example of a suitable oxidizable species is zinc and a suitable reducible species is silver chloride. While this combination may be advantageous for many applications, it is not meant as a limitation as the scope of the invention but is presented only by way of example.

During the iontophoretic process of this invention, as current flows, the oxidizable species in the cationic drug chamber and one or more intermediate cells become oxidized, while the reducible species in the anionic chamber and intermediate cells become reduced. The galvanically induced current will continue to flow until depletion of either the oxidizable or reducible species, whichever is present in limiting amount. The relationship between the amount of current flow and the amount of oxidizable or reducible species in limiting supply, is theoretically represented by Faradays constant; one gram equivalent of the limiting reducible or oxidizable species will provide one Faraday (96,487 coulombs) of electricity. The iontophoretic patch of this invention will optimally deliver a fixed and known charge in a range between about 0.06 and 60 coulombs, which corresponds to between 0.00000062 and 0.00062 gram equivalent weight of oxidizable or reducible species in limiting supply.

Preparation of the iontophoretic electrodes of this invention is critical, as a known limiting amount of electroactive species must be incorporated within, or onto, any anode electrode, any cathode electrode, or multiple electrodes. In preparation of the cationic drug chamber electrode, oxidizable material can be used of known weight and purity; or an oxidizable coating of known amount can be deposited on the surface of an electrically conductive substrate. For example, a known amount of molten zinc can be deposited over a wire substrate, to produce an electrode with known oxidizable species content. In preparation of the anionic drug chamber electrode, a reducible material of known amount can be deposited on the surface of an electrically conductive substrate. For example, a known amount of molten silver chloride can be deposited over a wire substrate, to produce an electrode with known reducible species content. Alternatively, a known amount of silver chloride can be generated on the electrode surface by an electrolytic or electroplating process, such as by electrolytic oxidation of a silver wire in the presence of chloride, to produce a coating of silver chloride.

The preferred approach to preparation of the iontophoretic electrodes of this invention is by screen printing of thin coatings, having known amounts of electroactive materials, over a conductive trace on a flexible substrate. This process yields a controlled dosage galvanic battery, for incorporation into the iontophoretic patch. Other circuit elements may also, be created using thin film, screen printing or other such methods in accordance with state-of-the-art techniques.

Other aspects of the patch include an impervious backing material, which can be constructed with 3M polyethylene tape #1523, #1526, (available from 3M Corporation, St. Paul, Minn.) or other occlusive material. Holding the electrodes in place, and attached to the backing material is a cell wall defining layer, which has separated openings to define anode and cathode cell cavities, as well as intermediate chamber cavities. The cell wall defining layer can be constructed of 3M #1772 or similar material. An absorbent layer is added to each of the cavities defined by the cell wall defining layer, and serves to retain fluid in the cell cavity. The absorbent layer can be a material which forms a gel when contacted with aqueous solution such as polyacrylamide, or it can be cotton, gauze, or other hydrophilic material. An adhesive layer is used to fix the iontophoretic device to the skin, which can also be comprised of materials such as 3M #1523 or #1526.

To use the controlled dosage iontophoresing device, solution containing cation to be delivered is put into the cationic drug chamber, and solution containing anion material is injected into the anionic drug chamber. The intermediate chamber is preferably filled with a conductive salt solution, through an access port on either the top or bottom of the device. Optionally, the intermediate chamber can be pre-filled with a salt-containing gel or paste. Unlike the Anionic and Cationic Drug Chambers, the intermediate chamber or source or sources should not be in contact with the skin. The patch is then applied to the portion of the body where drug is to be administered, and adhered to the skin by an adhesive layer on the bottom of the patch and or by an overlaying bandage material. Once contacted with skin, an electrical circuit is completed which allows passage of current and delivery of drug compounds.

DETAILED DESCRIPTION

Figure 1:
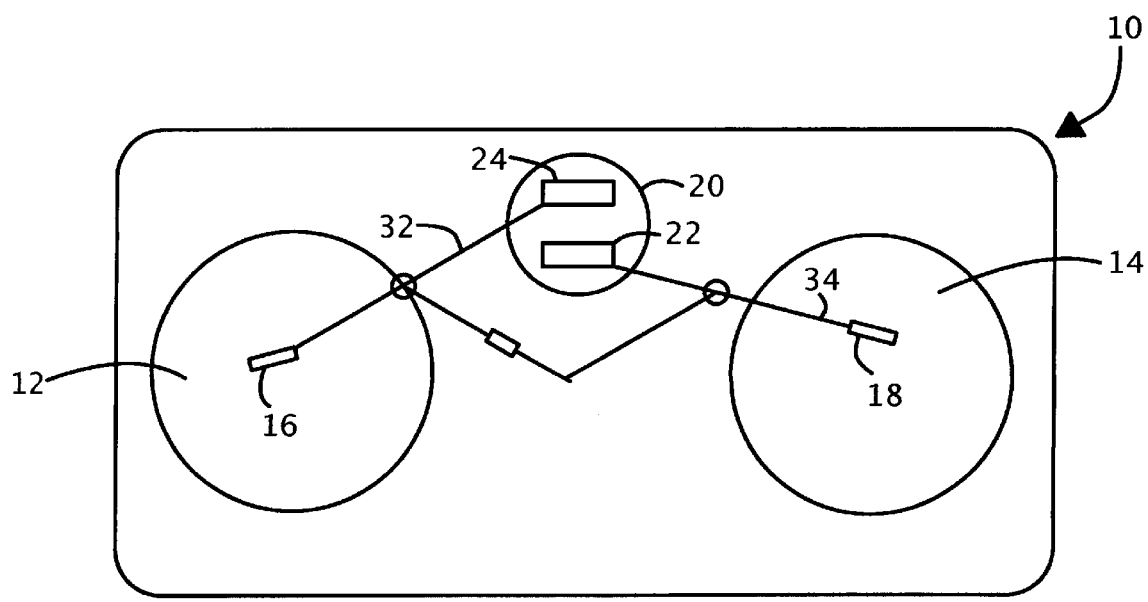
FIG. 1 is a schematic illustration of a galvanic iontophoretic system in accordance with the invention having a primary galvanic couple or source and one intermediate chamber having a second galvanic couple or source.

The detailed description of the present invention illustrates the principles of an advanced multi-source, multi-rate galvanic transdermal drug delivery system which has the ability to use time varying rates. The embodiments are described by using a very limited number of example configurations and material compositions, including therapeutic agents delivered. It is believed that the application of the principles encompassed by the present inventive concept, however, are much broader and, in reality, many configurations of primary and intermediate or therapeutic agent containing or additional galvanic sources or chambers, resistor elements or devices and other circuit elements together with a great number of conductors, galvanic couples (oxidizable and reducible species), therapeutic agents to be delivered and actual configurations of the wearable patch are possible. Accordingly, the descriptions and accounts given herein are intended as examples and not meant to limit the scope of the invention in any manner. Terms such as galvanic source, galvanic chamber, galvanic couple, are used interchangeably.

FIGS. 1, 2 and 6–9 of the drawings are intended to depict schematically some iontophoretic systems illustrating principles of the multi-source, multi-rate, time-variable, galvanic concept of the invention. A schematic representation of an iontophoretic wearable patch is shown at 10 which includes a primary dual chamber galvanic couple including a cationic drug chamber 12 and an anionic drug chamber 14. The cationic chamber 12 contains a source of oxidizable material 16, which may be zinc; and the anionic chamber contains a source of reducible material 18, which may be silver chloride. A first additional or intermediate chamber or source 20 is located between chambers 12 and 14, itself containing a source of oxidizable material 22, which may be the same (Zn) or a different material from the material 16 and a source of reducible material 24, which may be the same (AgCl) or a different material from the material 18. These are contained in a conductive relation in the intermediate chamber.

Figure 2:
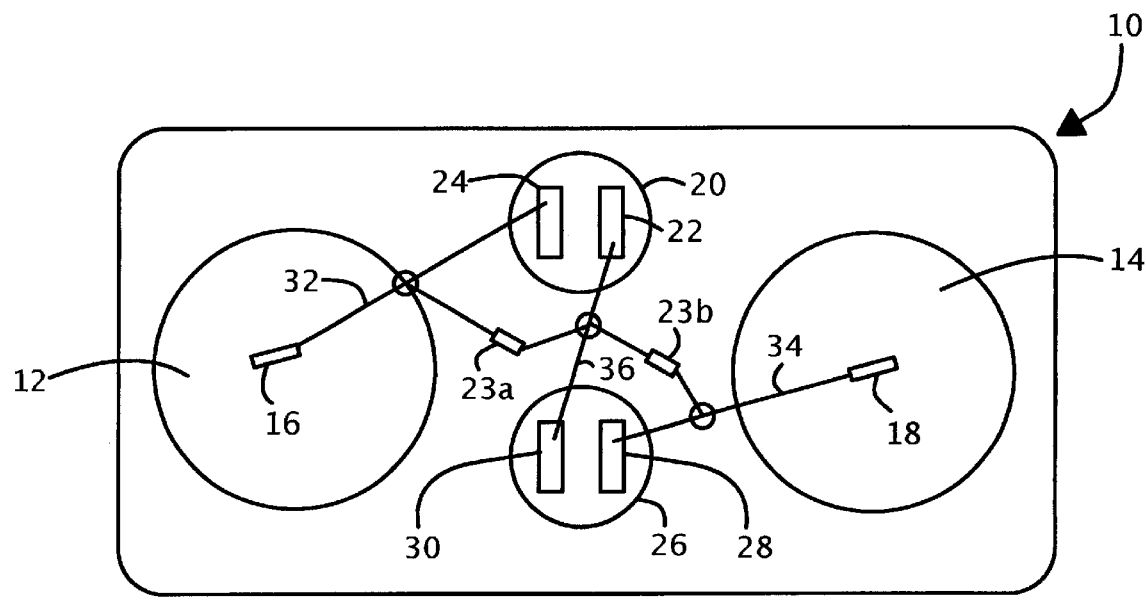
FIG. 2 is a schematic illustration of a galvanic iontophoretic system similar to that of FIG. 1 having a primary galvanic couple or source and two intermediate chambers or sources.

FIG. 2 shows the iontophoretic system of FIG. 1, but including a second intermediate chamber 26 containing a source of oxidizable material 28 and a source of reducible material 30 which may be the same as or different from those used in intermediate chamber 20. Conductors 32, 34 conduct the chambers 12, 20 and 18 in series in FIG. 1. An additional intermediate conductor 36 is provided in FIG. 2 to serially connect the intermediate chambers 20 and 26. An optional resistor device 23 is shown connected in phantom between conductors 32 and 34 in FIG. 1 in parallel with the galvanic sources (12, 14) and 20 and a pair of optional resistive devices 23a and 23b are shown connected in parallel with the two intermediate sources 20 and 26 in FIG. 2. If used the resistors cause the sources to operate in series while all sources are active and provide continuity to the circuit when the parallel connected source becomes depleted. The value of example resistor devices 23, 23a and 23b can be as desired but may typically be about equal to skin resistance or generally in the 1 K ohm to 100 K ohm range and typically about 10 K ohm.

Figure 7A:
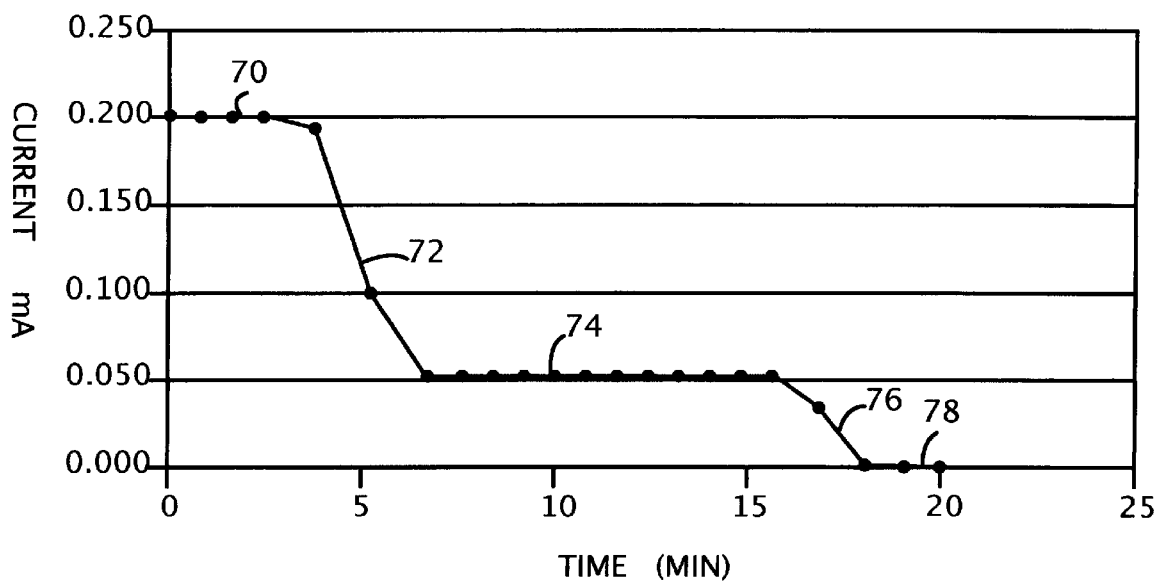
FIGS. 7a and 7b depict a graphical representation and circuit schematic of using one additional source and a parallel resistance approximating skin resistancy.
Figure 7B:
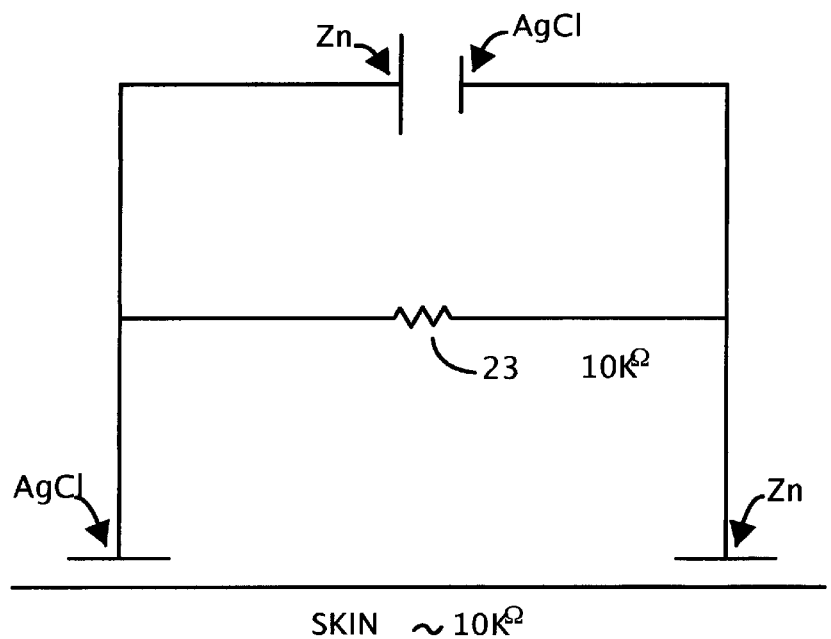

FIG. 7b depicts a simple circuit schematic for the schematic iontophoresis device illustrated in FIG. 1 in which the resistance 23 is approximately 10 Kohms which is generally equivalent to the average skin resistance experienced by patch devices used for iontophoretic transfer.

FIG. 7a graphically represents the operation of the schematic device illustrated in FIG. 7b, note the high initial delivery bolus 70 which rapidly diminishes at 72 with the depletion of the couple 22/24 at 72 to a value at 74 approximately ¼ of the original value and as much as the potential has been cut in half and the resistance double when the serial resistor 23 is added in. Another deep drop-off occurs at 76 when the couple 16, 18 is depleted and the transmission quickly falls to 0 at 78. This, then, illustrates one embodiment in which a higher dosage of medication is administered at the outset or beginning of a treatment followed by a lower dosage for a longer period of time. This drug delivery profile is appropriate for an application where it is desirable to reach a therapeutic level as quickly as possible in the body followed by a lower drug delivery rate that is adequate to maintain a drug level in the body just slightly above the therapeutic level for a longer period of time.

Figure 9:
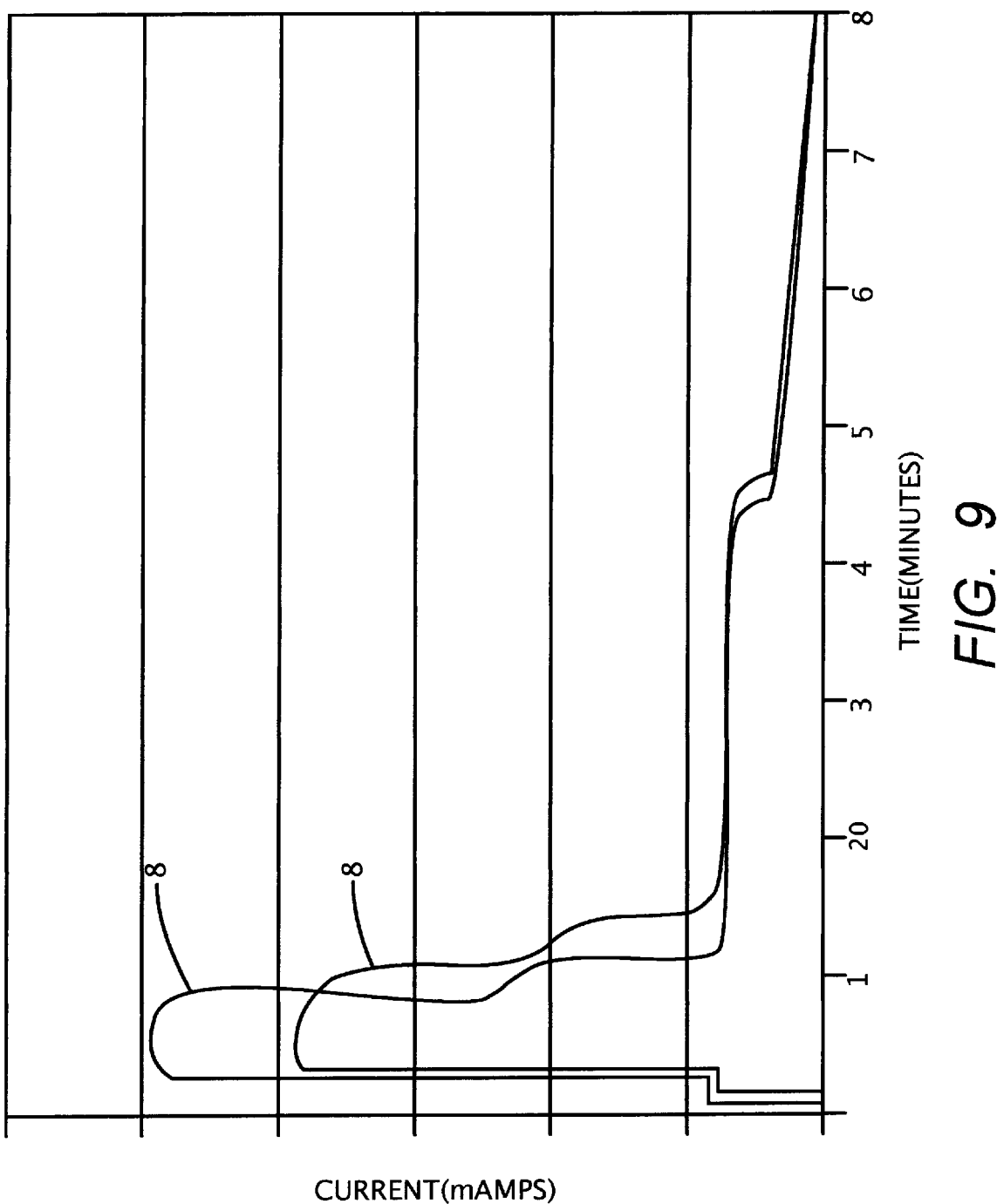
FIG. 9 represents actual laboratory data taken using the configuration of FIG. 7b.

FIG. 9 represents actual laboratory data derived form a configuration similar to that shown in FIGS. 1 and 7b. While there are certain differences between the curves 80 and 82 in that figure, they clearly indicate the administration of the initial bolus of higher rate of infusion followed by a longer period of at a lower rate and finally by an extinguishments of the current flow.

Figure 8A:
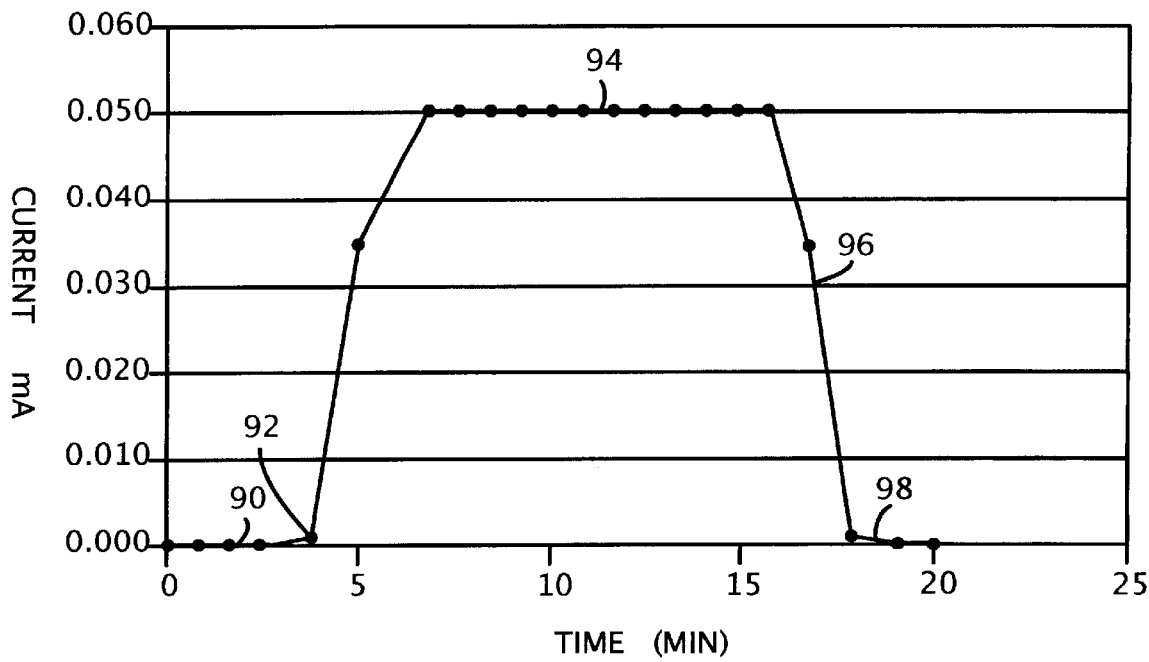
FIGS. 8a and 8b are similar to FIGS. 7a and 7b for a configuration in which the polarities of the sources are opposed.
Figure 8B:
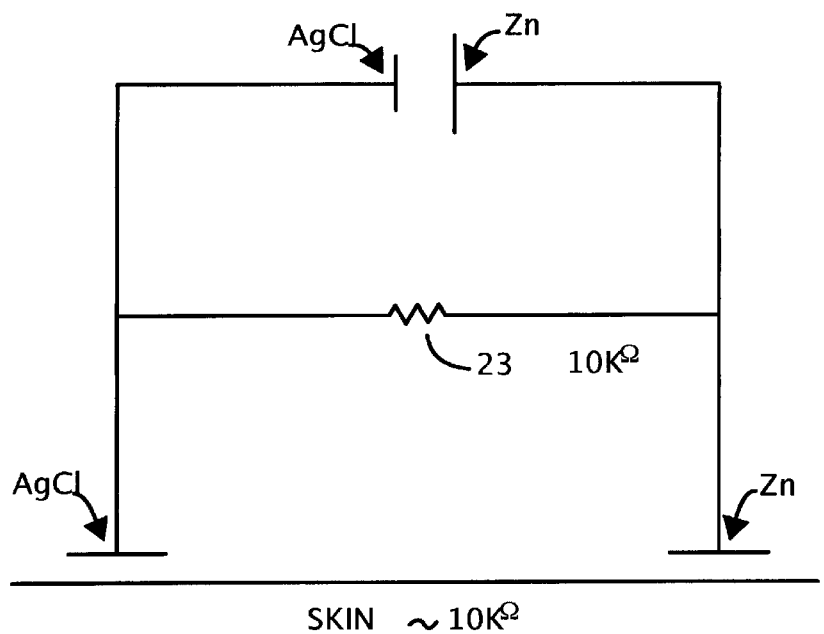

Finally we see FIG. 8b representing a circuit similar to those of FIG. 1 and FIG. 7b except that the second or additional source 22, 24 is connected in opposite polarity so that current generated by 22, 24 opposes that generated by 16, 18 as shown at 90 in FIG. 8a, this results initially in the absence of net current flow in the skin connected branch of the circuit such that no iontophoretic transfer takes place until the depletion of the anode or cathode of couple 22, 24 at 92 after which the delivery current rapidly rises to 0.05 mA where it remains substantially constant throughout the remainder of the life primary or agent delivering couple 16, 18 at 94. The depletion of an electrode in the agent delivering couple 16/18, the current again rapidly drops at 96 to 0 at 98.

It becomes apparent even from the small number of examples presented that one skilled in the art could arrive at a great many variations in electronic circuit design to construct a circuit that would produce almost any imaginable drug delivery profile one would desire based on the current-time profiles possible. Thus, series and parallel combinations are possible with almost any number of cells and resistors, keeping in mind that the cells can have different coulombic capacities and external resistances can be varied. It should further be noted that additional time can be added to the delivery by using additional cells in parallel rather than in series.

Figure 3:
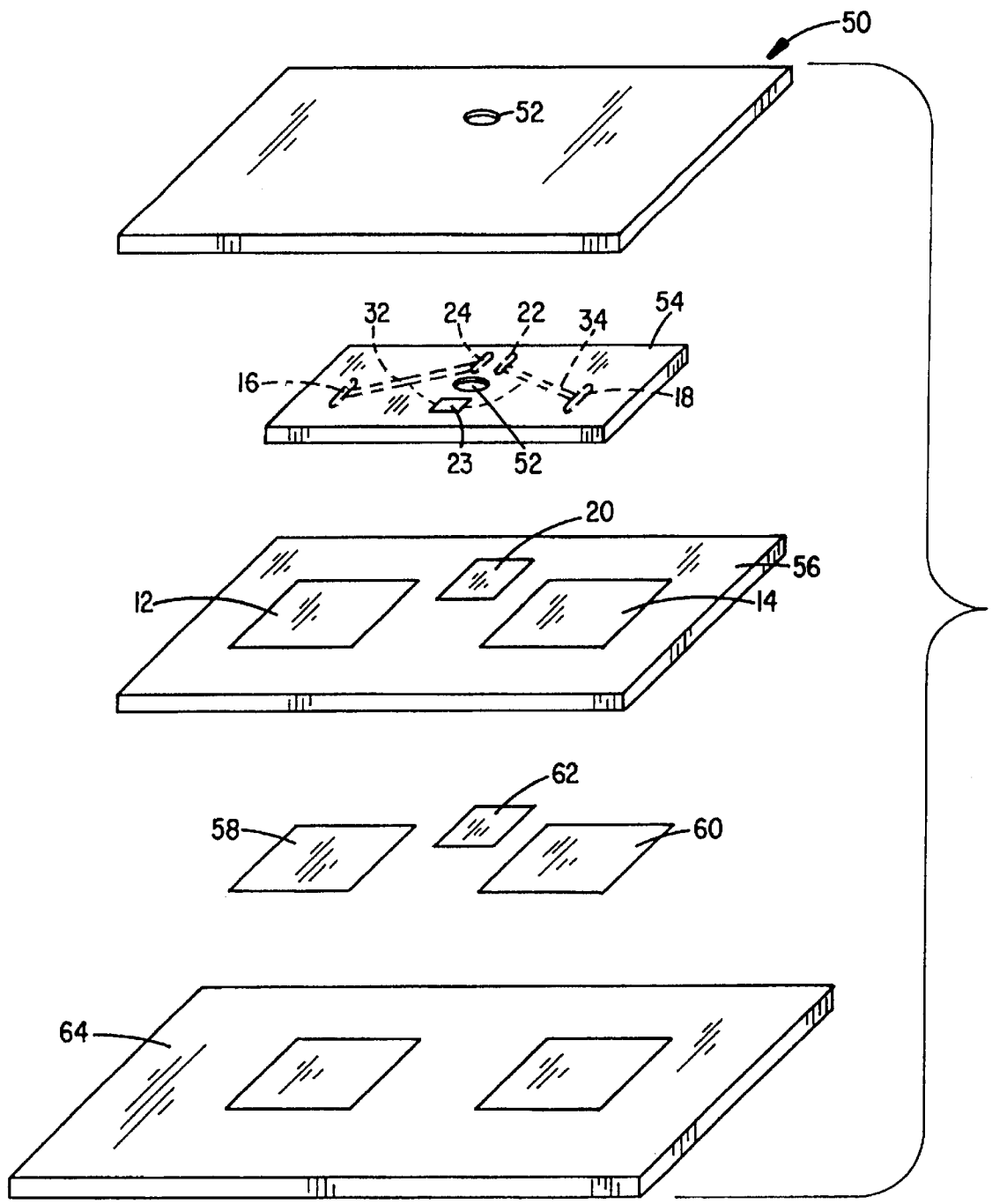
FIG. 3 is an exploded or blown apart drawing showing the assembly of an iontophoretic patch embodiment that includes a screen printed circuit system for an embodiment similar to that in FIG. 1.

The exploded view of FIG. 3 illustrates one preferred approach to the preparation of the iontophoretic electrode and conductor system for an embodiment similar to that illustrated in FIG. 1. It includes a layer of backing material layer 50, which may be constructed with material such as 3M polyethylene tape #1523, #1526 or other such occlusive membrane, an intermediate cell fill port is shown at 52. A dual galvanic source battery system is shown printed on a flex circuit screen layer 54 beneath the backing layer 50. A cell wall defining layer is shown at 56 and absorbent layers for the chambers are shown at 58, 60 and 62. The final bottom adhesive layer is shown at 64.

Figure 4:
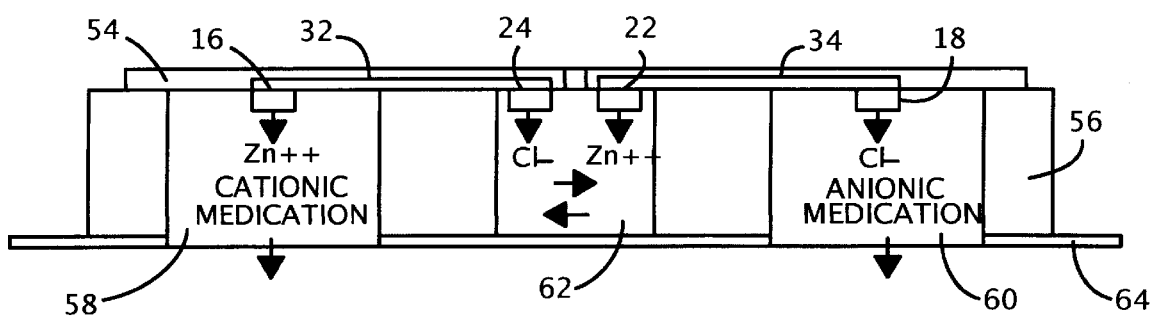
FIG. 4 shows, in crossection, a schematic illustration of ion flow in a one intermediate source version of the invention similar also to that in FIG. 1.

The cross sectional drawing of FIG. 4 illustrates the flow of electrons and ions during use of a one intermediate chamber version of this invention similar to that represented by FIG. 1 and so the same reference numerals can be employed. The intermediate chamber or source 20 may have a useful life that is the same as or shorter than that of the primary couple 12, 14. In this manner, the intermediate source 20 will boost the rate of transfer by the primary couple 12, 14 will control the amount such that when either the oxidizable material of the cationic drug chamber electrode 16 is depleted, or the reducible material of the anionic drug chamber electrode 18 is depleted, current flow falls to essentially zero and the delivery of drug compound is completed.

Figure 5:
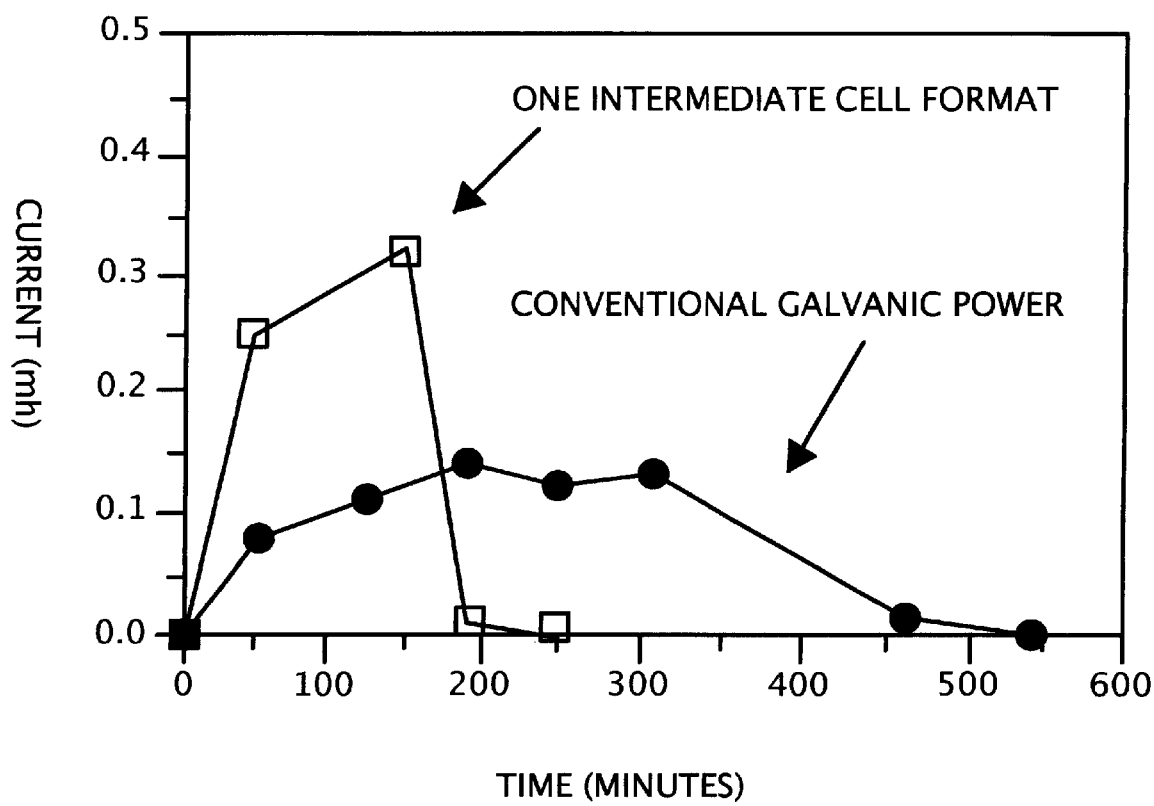
FIG. 5 shows comparison current-time profile plot between a one intermediate source version of the present invention and a conventional galvanic system without an intermediate galvanic source.

FIG. 5 illustrates the fixed delivery of current as a function of time from a battery prepared in accordance to this invention. In this experiment, a limiting supply of zinc serves as the oxidizable species, the reducible species was silver chloride, and one intermediate cell was used. For comparison purposes, a current-time profile of a conventional galvanic system is charted as well, also using zinc as an oxidizable species in limiting supply and silver chloride as the reducible species. As shown, the current level (and consequently the medication delivery rate) is higher in this invention, owing to a higher application voltage (2 volts vs. 1 volt).

Figure 6:
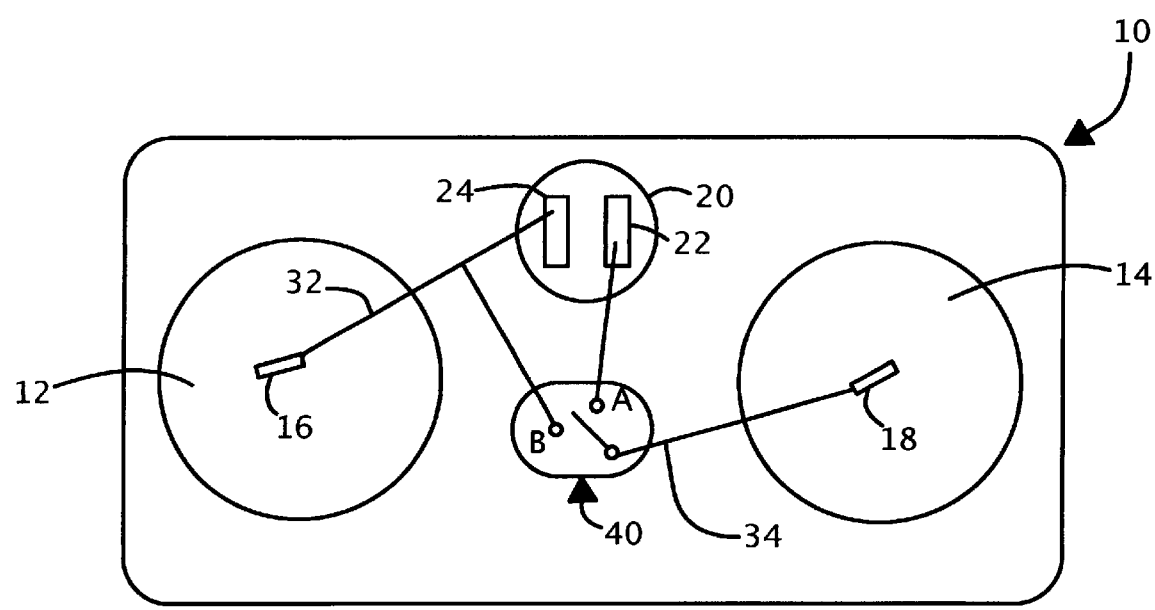
FIG. 6 shows an illustration including a switch mechanism in conjunction with the system of FIG. 1 to enable manually adjustable higher and lower voltage activation and an off setting.

FIG. 6 is an illustration of the invention similar to FIG. 1 with an integrated switch, again using zinc and silver chloride as the oxidizable and reducible species. Activation of the switch in "A" position allows a high application voltage (in this case to 2 volts) and higher medication flow. Adjustment of the switch to the "B" position reduces voltage (in this case to 1 volt) and to a lower medication flow. In addition, this shows how this invention can be modified to allow manual adjustment of medication flow between high and low flow rates with a simple switch assembly. In addition, the current flow may be shut off in the illustrated neutral position.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A transdermal iontophoretic therapeutic agent delivery system comprising;
   (a) a plurality of self-contained, serially connected galvanic power sources, wherein said plurality of galvanic power sources alone provide the power for the device and the control for the rate and dosage of therapeutic agent delivered;
   (b) wherein said plurality of galvanic power sources are unequal in columbic capacity such that at least one of said galvanic power sources is depleted earlier than the others; and
   (c) a resistance device connected in parallel with one or more of said plurality of galvanic power sources.

2. An iontophoretic system as in claim 1 wherein one or more of said galvanic power sources are of a coulombic capacity corresponding to a predetermined dosage rating.

3. An iontophoretic system as in claim 1 wherein one or more of said plurality of galvanic power sources has electrodes prepared using screen-printing.

4. A transdermal iontophoretic therapeutic agent delivery system comprising:
   (a) a plurality of self-contained, serially connected galvanic power sources, wherein said plurality of galvanic power sources alone provide the power for the device and the control for the rate and dosage of therapeutic agent delivered;
   (b) wherein said plurality of galvanic power sources are unequal in columbic capacity such that at least one of said galvanic power sources is depleted earlier than the others; and
   (c) wherein a pair of said galvanic power sources are connected in opposed polar relation and connected in parallel with a resistor device such that net iontophoretic delivery current flows to deliver said therapeutic agent only after said source of lower coulombic capacity is depleted.

5. An iontophoretic system as in claim 4 wherein one or more of said galvanic power sources are of a coulombic capacity corresponding to a predetermined dosage rating.

6. An iontophoretic system as in claim 4 wherein one or more of said plurality of galvanic power sources has electrodes prepared using screen-printing.

7. An iontophoretic system for transdermal delivery of a therapeutic agent, comprising
   (a) a plurality of galvanic power sources, each containing an oxidizable species and a reducible species, wherein said plurality of galvanic power sources alone provide the power for the device and the control for rate and dosage of therapeutic agent delivered;
   (b) wherein at least one of said plurality of galvanic power sources is a therapeutic agent dispensing power source for receiving and dispensing a therapeutic agent further comprising,
      (1) an oxidizable species in contact with a first delivery chamber for containing a therapeutic agent,
      (2) a reducible species in contact with a second delivery chamber for containing a therapeutic agent;
   (c) conductors serially connecting said plurality of galvanic power sources such that an overall galvanic potential of said transdermal iontophoretic delivery system is the sum of said galvanic power sources;
   (d) wherein said plurality of galvanic power sources includes one or more sources of significantly lower coulombic capacity than at least one other galvanic power source to provide for earlier depletion;
   (e) at least one resistor device connected in parallel with one or more of said plurality of serially connected galvanic power sources of unequal coulombic capacity;
   (f) wherein a pair of said serially connected galvanic power sources include a therapeutic agent dispensing source and a second source wherein the therapeutic agent dispensing power source has a higher coulombic capacity than said second power source; and
   (g) wherein the serially connected therapeutic agent dispensing power source and another galvanic power source are connected in opposed polarity so that there is no net current flow until said second power source is depleted.

8. A delivery system as in claim 7 wherein said oxidizable species in each of said galvanic power sources is the same.

9. A delivery system as in claim 7 wherein said reducible species in each of said galvanic power sources is the same.

10. A delivery system as in claim 7 wherein all said oxidizable species are the same species and all said reducible species are the same species.

11. A delivery system as in claim 7 wherein said control includes the provision of a predetermined charge capacity for at least one of said galvanic power sources based on adjusting the amount of one or both of said oxidizable and said reducible species provided.

12. A delivery system as in claim 7 wherein said oxidizable species is selected from Mg and Zn and said reducible species is AgCl.

13. An iontophoretic system for transdermal delivery of a therapeutic agent, comprising:
   (a) a plurality of galvanic power sources, each containing an oxidizable species and a reducible species, wherein said plurality of galvanic power sources alone provide the power for the device and the control for rate and dosage of therapeutic agent delivered
   (b) wherein at least one of said plurality of galvanic power sources is a therapeutic agent dispensing power source for receiving and dispensing a therapeutic agent further comprising,
      (1) an oxidizable species in contact with a first delivery chamber for containing a therapeutic agent,
      (2) a reducible species in contact with a second delivery chamber for containing a therapeutic agent;
   (c) conductors serially connecting said plurality galvanic sources that an overall galvanic potential of said transdermal iontophoretic delivery system is the sum of said galvanic power sources; and
   (d) switch means for selectively by-passing one or more power sources serially connected with said therapeutic agent dispensing power source to enable a user to select desired delivery potential.

14. A delivery system as in claim 13 wherein said oxidizable species in each of said galvanic power sources is the same.

15. A delivery system as in claim 13 wherein said reducible species in each of said galvanic power sources is the same.

16. A delivery system as in claim 13 wherein all said oxidizable species are the same species and all said reducible species are the same species.

17. A delivery system as in claim 13 wherein said control includes the provision of a predetermined charge capacity for at least one of said galvanic power sources based on adjusting the amount of one or both of said oxidizable and said reducible species provided.

18. A delivery system as in claim 13 wherein said oxidizable species is selected from Mg and Zn and said reducible species is AgCl.

* * * * *